United States Patent [19]

Healy et al.

[11] 4,029,717

[45] June 14, 1977

[54] SIMULATED MOVING BED ADSORPTION-DESORPTION PROCESS FOR PARAXYLENE RECOVERY

[75] Inventors: Frank J. Healy, Morristown; Paul R. Geissler, Edison, both of N.J.

[73] Assignee: Exxon Research and Engineering Company, Linden, N.J.

[22] Filed: Mar. 7, 1975

[21] Appl. No.: 556,431

Related U.S. Application Data

[63] Continuation-in-part of Ser. No. 457,056, April 1, 1974, abandoned.

[52] U.S. Cl. .................... 260/674 SA; 208/310 Z; 210/31 C
[51] Int. Cl.² .................... C07C 7/13; C10G 25/04; B01D 15/08
[58] Field of Search .......... 260/674 SA; 208/310 Z; 210/31 C

[56] References Cited

UNITED STATES PATENTS

| | | | |
|---|---|---|---|
| 3,201,491 | 8/1965 | Stine et al. | 260/674 |
| 3,455,815 | 7/1969 | Fickel | 208/310 |
| 3,696,107 | 10/1972 | Neuzil | 260/674 |
| 3,715,409 | 2/1973 | Broughton | 260/674 |
| 3,732,325 | 5/1973 | Pharis et al. | 260/674 |
| 3,733,261 | 5/1973 | Adams et al. | 208/310 |
| 3,761,533 | 9/1973 | Otani et al. | 260/674 |
| 3,835,043 | 9/1974 | Geissler et al. | 210/31 |

*Primary Examiner*—Delbert E. Gantz
*Assistant Examiner*—G. E. Schmitkons
*Attorney, Agent, or Firm*—F. A. Santoro; C. Leon Kim

[57] ABSTRACT

Simulated moving bed processes for the separation of $C_8$ aromatic isomers using molecular sieve adsorbents are improved by the use of meta-diisopropylbenzene as the eluting agent. The invention describes a process for continuously separating, in a liquid phase, components of the feed mixture by contacting said feed mixture with a solid sorbent and utilizing a simulated countercurrent flow system wherein a liquid stream flows through serially and circularly interconnected desorption, rectification and sorption zones. In such a process the flow of liquid stream is interrupted between both the desorption and rectification zones and a first portion of effluent from the desorption zone, a portion being rich in sorbate may be directly circulated and a second portion, the same comprising sorbate of high purity and desorbent may be fed to a distillation apparatus from which one portion of the sorbate distillate may be circulated as reflux to the rectification zone to maximize the sorbate product purity at reduced costs and another portion is recovered as product. The present improved process is conducted using meta-diisopropylbenzene as a desorbent either alone or in combination with inert diluents such as paraffins. This embodiment provides a more effective separation of paraxylene and ethylbenzene peaks, thus increasing paraxylene recovery and at the same time reducing the amount of recycle and further ethylbenzene-paraxylene separations such as distillations and the like. This better separation allows more efficient use of the adsorbent bed and/or lower ratios of eluting materials to $C_8$ aromatic feed which results in a more economic process.

10 Claims, 4 Drawing Figures

FIGURE I

ADSORPTION DESORPTION PROCESS

FIGURE 2

DUAL DESORBENT COMPOSITION

FIGURE 3

DUAL TEMPERATURE

FIGURE 4

DUAL TEMPERATURE – COMPOSITION

SIMULATED MOVING BED ADSORPTION-DESORPTION PROCESS FOR PARAXYLENE RECOVERY

CROSS-REFERENCE TO RELATED APPLICATION

This application is a Continuation-In-Part application of Ser. No. 457,056, filed Apr. 1, 1974. and now abandoned.

BACKGROUND OF THE INVENTION

This invention relates to improvements for a separation process which utilizes a simulated countercurrent flow system wherein a fluid stream flows through serially and circularly interconnected desorption, rectification and adsorption zones. More particularly, the improvements concern the use of meta-diisopropylbenzene as eluting agent either alone or in admixture with inert diluents such as paraffins. Thus it has been found that a distinct advantage results from the use of meta-diisorpropylbenzene since better separation of paraxylene from the other $C_8$ aromatic isomers is obtained than was previously obtainable with the use of prior art eluting agents such as toluene, diethylbenzenes and the like.

The present process employing the above embodiments is an improvement of the simulated countercurrent flow processes described in U.S. Pat. Nos. 3,761,533 and Pat. 3,201,491. It is known that adsorption-separation processes of liquid feed mixtures, the technique of employing a moving bed type adsorption process wherein said moving bed comprises adsorbent particles which are countercurrently contacted with streams of liquid feedstock and desorbent, results in a high degree of purity for the adsorbed product. This process and the so-called "simulated countercurrent flow system" wherein the solid sorbent particles are stationary have been proposed and disclosed in the above-referred to patents.

In the latter known process, an adsorption column is divided into three zones: the adsorption zone, a desorption zone, and a rectification zone. These zones are serially interconnected in order and a continuously circulated fluid stream flowing through the three zones is maintained by circulating the effluent fluid from an outlet of the last zone to an inlet of the first zone; all the points of introducing and withdrawing the inlet and outlet streams are simultaneously shifted, at stated intervals of time, in a downstream direction to provide thereby a simulated countercurrent flow system wherein there is achieved a processing effect similar to that observed in the moving bed type adsorption process, i.e. a high degree of purity of the sorbate product can be obtained from the stream of desorbent flowing throughout all the three zones at higher flow rate. This process for a simulated countercurrent flow system in an adsorption-separation process may be described as follows. In such a process, at least one of the components of the liquid feed mixture is selectively sorbed by contact with solid sorbent particles; said liquid feed mixture as liquid streams are allowed to flow through three serially and circularly interconnected zones; a desorption zone, a rectification zone and a sorption zone, each zone being divided into a plurality of serially interconnected sections, each section being packed with a mass of the solid sorbent particles; introducing desorbent into the first section of the desorption zone; introducing the liquid feed mixture to the first section of the sorption zone and withdrawing a raffinate effluent comprising a less sorbed component and the desorbent from the sorption zone; and all the points of introducing and withdrawing the liquid streams into and from the sections are simultaneously shifted, one section at a time, at stated intervals of time, in a downstream direction, while maintaining the same order of continuity and the same spatial relationship between all the points; interrupting the liquid streams flowing through the three zones at a point between the desorption zone and the rectification zone, while the first portion of the desorption effluent flowing out from the last section of the desorption zone, which portion contains either a little or no desorbent but contains the selectively sorbed component, is directly circulated, and the second portion thereof which portion contains the selectively sorbed component of high purity, but at a lower concentration in comparison with the first portion, is introduced into a distillation apparatus from which one portion of the sorbate distillate is circulated as reflux into the first section of the rectification zone and another portion is recovered as product. In conducting the above-described process for paraxylene separations from $C_8$ aromatic feedstreams, as well as other art processes similar to said process, any increase in paraxylene separation that may be affected by the use of particular eluting agents and/ or reduction of desorbent to feed ratios which can be obtained substantially enhances the efficiency of the process and lowers the cost of recovering the high purity sorbed component, i.e., paraxylene, and is, therefore, desirable.

SUMMARY OF THE INVENTION

In accordance with the present invention, simulated countercurrent flow adsorption-separation processes for parxylene separation from $C_8$ aromatic feedstreams as described above are operated with the use of meta-diisopropylbenzene as eluting agent either alone or in admixture with inert diluents such as paraffins. In such an inventive embodiment, the desorbent material consists of pure meta-diisopropylbenzene and/or meta-diisopropylbenzene in admixture with a paraffin such as n-dodecane. Meta-diisopropylbenzene as a desorbent serves to effectively elute paraxylene from the sorbent, and to promote an efficient separation of paraxylene from ethylbenzene, metaxylene and orthoxylene. Because of its improved ability to promote the separation, meta-diisopropylbenzene permits separation using less sorbent for a given quantity of feed, and/or operating under conditions which enable the two product streams using less total desorbent than is possible with other, less effective, desorbent liquids. In a commercial process to separate paraxylene, these advantages of less sorbent and/or less total desorbent would readily result in a more economically attractive process.

In a preferred embodiment, the improved process is applicable to the separation of paraxylene and/or paraxylene and ethylbenzene from $C_8$ aromatic isomer feedstreams. The separation of these isomers from a $C_8$ aromatic isomer feedstream may be carried out by utilizing particular crystalline metal aluminosilicate sorbent materials. Examples of crystalline metal aluminosilicate sorbents useful for the separation of xylenes by means of the present process include potassium substituted zeolite X or Y, barium substituted zeolite X or Y, barium and potassium substituted X or Y. Other useful crystalline metal aluminosilicate sorbents that may be employed in the present invention may be found described in copending application Ser. No. 282,983, filed Aug. 23, 1972 now U.S. Pat. No. 3,843,518 and U.S. Pat. Nos. 3,626,020, 3,732,325 and 3,734,974.

In this specification carrier fluid or diluent is taken as liquid materials which are not significantly adsorbed by the substrate in the presence of feed mixture components. Eluent, eluting agent and desorbent are terms to describe liquid materials which are adsorbed by the substrate and compete for adsorption sites with the feed components.

The desorbent useful in this invention is metadiisopropylbenzene and readily displaces most of the components of the $C_8$ aromatic feedstream except the paraxylene which is slightly more strongly adsorbed than it. Hence paraxylene is eluted last and results is more efficient paraxylene recovery. The stream which flows through the successive beds of the desorption zone however comprises a mixture of desorbent and desorbed sorbate released from an upstream bed of sorbent. When meta-diisorpropylbenzene is used alone as desorbent then paraxylene tailing is minimized. While not preferred, however, the meta-diisopropylbenzene is used in admixture with an inert diluent such as paraffins. Thus paraffins having from 10 to 20 carbon atoms, preferably from 11 to 18 carbon atoms are seen useful as diluents. Also useful are naphthenes which are saturated cyclic hydrocarbons with or without alkyl substituents and which have from 6 to 20 carbon atoms, preferably from 11 to 18 carbon atoms. When the inert diluent is employed with meta-diisorpropylbenzene, it is usually employed in amounts of from 1 to 90 wt. %., preferably from 1 to 60 wt. % and most preferably from 5 to 50 wt. %.

Figure 1:
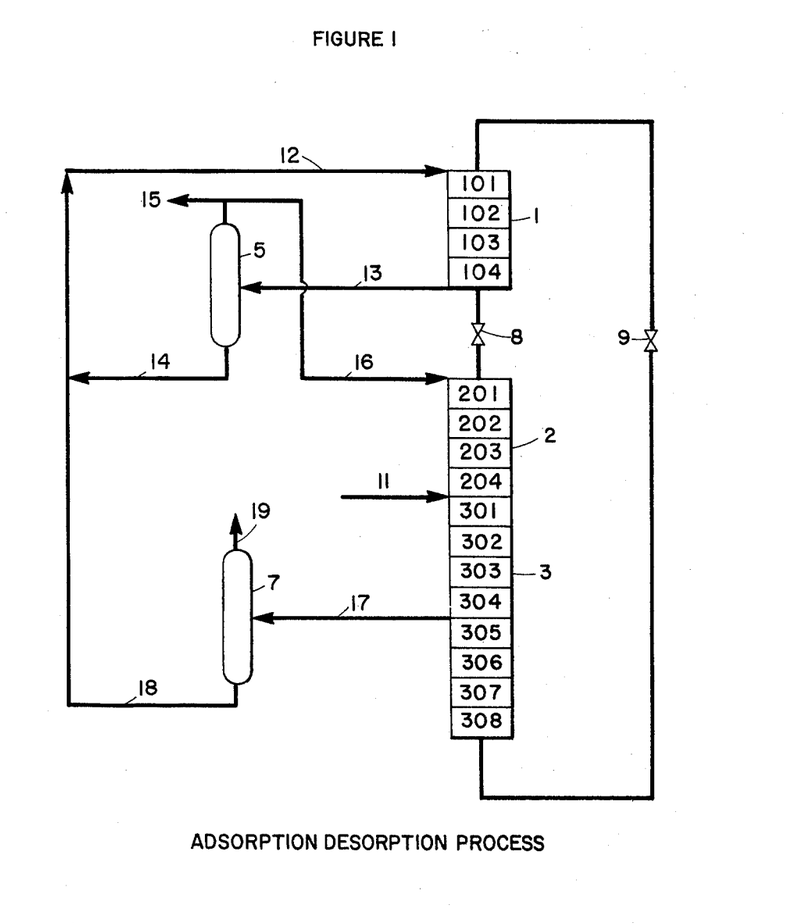

The invention and its embodiments will more easily be understood by reference to FIG. 1 attached hereto and made a part hereof. FIG. 1 shows a block diagram by which the process employing the novel desorbent is carried out.

As shown in FIG. 1, previous sorption-separation systems fundamentally involve solid sorbent particles-charged columns which are divided into three zones: 1 desorption zone, 2 rectification zone and 3 sorption zone. These zones are serially and circularly interconnected in order. Each zone is composed of a plurality of serially interconnected sections in the flow direction of liquid streams.

In the desorption zone 1, a sorbate component selectively sorbed onto solid sorbent particles is desorbed by contact with a desorbent stream. In the rectification zone 2, countercurrent contact between the stream of a sorbate product and a simulated flow of the solid sorbent particles is effected to maximize thereby the purity of the product. In the sorption zone 3, separation of a liquid feed mixture takes place by selective sorption of a sorbate component of the mixture by solid sorbent particles.

Flows of the various liquids are illustrated with reference to FIG. 1. Desorbent 12 flows into the desorption zone 1 through an inlet of the first section 101 of the zone while a liquid mixture 13 of desorbent and sorbate (the mixture is hereinafter referred to as "desorption effluent") is withdrawn through an outlet of the last section 104 of the desorption zone 1 and flows into a distillation column 5 wherein the desorption effluent is separated into both desorbent 14 and sorbate components. The desorbent 14 is circulated for re-use. One portion of the sorbate component 15 is withdrawn from the system as a product and the other portion flows 16 into the top section 201 of the rectification zone 2 as a reflux stream. A liquid free mixture 11 comprising at least one sorbate component flows through an inlet positioned between both the rectification and sorption zones into the sorption zone 3. A mixture 17 of desorbent and raffinate components, i.e., less sorbed components (which mixture is hereinafter referred to as "raffinate effluent" ) is withdrawn from section 304 of the sorption zone 3 and flows into a distillation column 7 wherein the raffinate effluent is separated into desorbent 18 and raffinate 19. When operated in the conventional manner, desorbent 18 is directly circulated for reuse as part of stream 12 and the raffinate 19 is withdrawn from the system. The liquid streams flowing through the three zones are interrupted at two points between both the desorption and rectification zones and both the sorption and desorption zones, respectively, by suitable interrupting means such as valves 8 and 9.

As in typical previous operations, the entire liquid stream flowing through the sorption zone 3 is divided into two portions, one portion being withdrawn 17 from the zone 3 as a raffinate effluent and the other portion allowed to flow directly down into the remaining sections (305, 306, 307, 308).

The number of the sections existing downstream from the withdrawal point of raffinate effluent 17 in the sorption zone 3 are determined as follows; the entire length of the sections from the withdrawal point to the bottom of the last section 308 in the sorption zone is such that a concentration of raffinate contained in the stream flowing down through these sections reaches approximately zero at the bottom of the last section 308.

Thus, the stream substantially containing no raffinate components is directly and continuously introduced through a valve 9 into the desorption zone.

The top sections 101, 201, 301 of the desorption, rectification and sorption zones are simultaneously transferred to the bottoms of the sorption, desorption and rectification zones, respectively, at stated intervals of time. The transfer is effected by shifting all the points of introducing and withdrawing of all the liquid streams (12, 13, 11 and 17) into and from the sorption column one step (i.e., one section) simultaneously in a downstream direction. Thus, a simulated countercurrent flow system is provided whereby the effects are obtainable similar to that achieved by a moving bed type sorption process wherein reflux streams come countercurrently into contact with fluid occupying the void spaces between sorbent particles, and the rectification action, going hand in hand with desorption action effected in the desorption zone, ensures the continuous preparation of the sorbate product of high purity.

In accordance with the present invention, simulated countercurrent flow adsorption-separation processes as described above are also operated with the dual desorbent composition technique of copending U.S. Ser. No. 457,056. In this inventive embodiment, the desorbent materials consist of meta-diisopropylbenzene, i.e., MDIPB, in two different concentrations to give different desorbent strength, with a diluent easily separable by some means such as distillation. The first desorbent $D_1$ (i.e., MDIPB) is more strongly adsorbed on the adsorbing agent than the most strongly adsorbed product, while the second desorbent $D_2$ (i.e. diluted MDIPB) is less strongly adsorbed than $D_1$ and is preferentially intermediate in strength between the most strongly adsorbed product and the weakly adsorbed product. $D_2$ consists of the same principal material as $D_1$ (i.e., MDIPB) but is made less strongly adsorbing by dilution with a weakly adsorbed or unadsorbed material, such as a paraffin.

In another separate embodiment of the present invention, the simulated countercurrent separation processes are improved further by the use of a temperature gradient technique. This procedure comprises utilizing temperature to increase the efficiency of the desorbent employed. It has been discovered that by preheating the desorbent to higher temperatures prior to its introduction to the desorption zone, such as with a heat exchanger or some other means, that the desorbent strength as a desorbent is significantly increased. By use of this embodiment, therefore, higher temperatures in the desorption zone permit the use of smaller amounts of desorbent than would be required at lower temperatures. Simultaneously, in accordance with this embodiment, lower temperatures are employed in the rectification and adsorption zones to permit easy adsorption of the feed; the latter thereby optimizes the purification of the more strongly adsorbed product in the former. This improvement may be carried out by the use of a heat exchanger to remove any residual heat from the desorbent before it passes to the rectification zone.

In a further embodiment, the simulated countercurrent flow separation process may be operated by combining both the dual desorbent composition and dual temperature techniques. This embodiment utilizes a weaker desorbent $D_2$ in the sorption and rectification zones and a stronger desorbent $D_1$ in the desorption zone, with $D_1$ being at a higher temperature than $D_2$. The result of the combination would be a much greater saving of necessary desorbent and in many cases result in greater reduction in cost than either of the embodiments effected separately.

Figure 2:
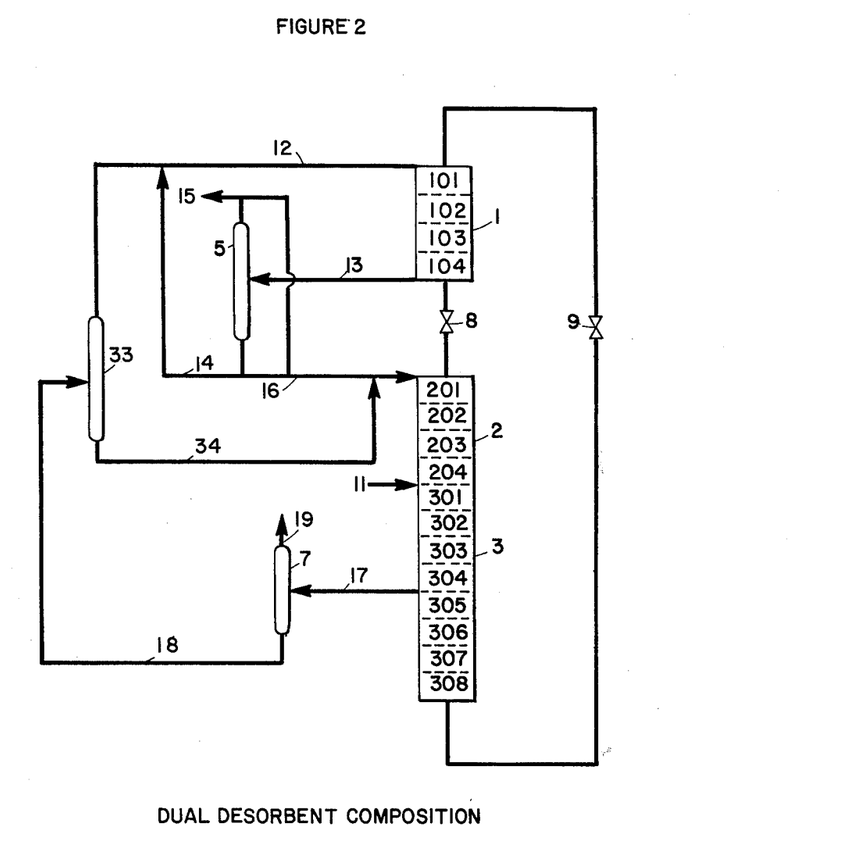

The desorbent described above is generally a material capable of displacing sorbate component of the feedstock already adsorbed on the solid sorbent when the beds now comprising the desorption zone were in the sorption zone of a previous cycle of operation. The stream flowing through the successive beds of the desorption zone thus comprises a mixture of desorbent and desorbed sorbate released from an upstream bed of sorbent. The preferred desorbents as disclosed in this invention consists of pure meta-diisopropylbenzene and meta-diisopropylbenzene in admixture with a paraffin such as dodecane in the process operated as a $C_8$ aromatic isomer separation process. This application of the invention and its embodiments will more easily be understood by reference to FIGS. 2 and 3 attached hereto and made a part hereof. FIG. 2 shows a block diagram in which the dual desorbent composition embodiment is carried out.

As shown in FIG. 2, previous sorption-separation systems fundamentally involve solid sorbent particles charged columns which are divided into three zones: 1 desorption zone, 2 rectification zone and 3 sorption zone. These zones are serially and circularly interconnected in order. Each zone is composed of a plurality of serially interconnected sections in the flow direction of liquid streams.

In the desorption zone 1, a sorbate component selectively sorbed onto solid sorbent particles is desorbed by contact with a desorbent stream. In the rectification zone 2, countercurrent contact between the stream of a sorbate product and a simulated flow of the solid sorbent particles is effected to maximize thereby the purity of the product. In the sorption zone 3, separation of a liquid feed mixture takes place by selective sorption of a sorbate component of the mixture by solid sorbent particles.

Flows of the various liquids are illustrated with reference to FIG. 2. Desorbent 12 flows into the desorption zone 1 through an inlet of the first section 101 of the zone while a liquid mixture 13 of desorbent and sorbate (the mixture is hereinafter referred to as "desorption effluent") is withdrawn through an outlet of the last section 104 of the desorption zone 1 and flows into a distillation column 5 wherein the desorption effluent is separated into both desorbent 14 and sorbate components. The desorbent 14 is circulated for reuse, as hereinafter more specifically illustrated. One portion of the sorbate component 15 is withdrawn from the system as a product and the other portion flows 16 into the top section 201 of the rectification zone 2 as a reflux stream. A liquid feed mixture 11 comprising at least one sorbate component flows through an inlet positioned between both the rectification and sorption zones into the sorption zone 3. A mixture 17 of desorbent and raffinate components, i.e., less sorbed components (which mixture is hereinafter referred to as "raffinate effluent") is withdrawn from section 304 of the sorption zone and flows into a distillation column 7 wherein the raffinate effluent is separated into desorbent 18 and raffinate 19. When operated in the previously taught manner, desorbent 18 is directly circulated for reuse as part of stream 12 (contrary to the scheme as shown in FIG. 1) and the raffinate 19 is withdrawn from the system. The liquid streams flowing through the three zones are interrupted at two points between both the desorption and rectification zones and both the sorption and desorption zones, respectively, by suitable interrupting means such as valves 8 and 9.

In typical previous operations, the entire liquid stream flowing through the sorption zone 3 is divided into two portions, one portion being withdrawn 17 from the zone 3 as a raffinate effluent and the other portion allowed to flow directly down into the remaining sections (305, 306, 307, 308).

The number of the sections existing downstream from the withdrawal point of raffinate effluent 17 in the sorption zone 3 are determined as follows; the entire length of the sections from the withdrawal point to the bottom of the last section 308 in the sorption zone is such that a concentration of raffinate contained in the stream flowing down through these sections reaches approximately zero at the bottom of the last section 308.

Thus, the stream substantially containing no raffinate components is directly and continuously introduced through a valve 9 into the desorption zone.

The top sections 101, 201, 301 of the desorption, rectification and sorption zones are simultaneously transferred to the bottoms of the sorption, desorption and rectification zones, respectively, at stated intervals of time. The transfer is effected by shifting all the points of introducing and withdrawing of all the liquid streams (12, 13, 11 and 17) into and from the sorption column one step (i.e., one section) simultaneously in a downstream direction. Thus, a simulated countercurrent flow system is provided whereby the effects are obtainable similar to that achieved by a moving bed type sorption process wherein reflux streams come countercurrently into contact with fluid occupying the void spaces between sorbent particles, and the rectification action, going hand in hand with desorption action effected in the desorption zone, ensures the continuous preparation of the sorbate product of high purity.

In the present improvement as shown in FIG. 2, desorbent stream 18 from distillation column 7 is separated in distillation column 33 into a strong desorbent stream 12 and a weaker desorbent stream 34. Stream 12 and Stream 14, consisting of strong desorbent from distillation column 5, flow into the first section of the desorption zone 1, where because of its high strength, a small quantity is sufficient to desorb all the most strongly adsorbed product. Weak desorbent Stream 34 flows into the first section of the rectification zone 2, along with reflux stream 16. In zone 2, the weaker desorbent acts to remove any of the weakly adsorbed products, while its strength is not sufficient to remove the most strongly adsorbed product. The use of the two desorbent streams of different strengths, therefore, minimizes the total amount of desorbent required by using a strong desorbent stream in the desorption zone and a suitable weaker desorbent to achieve the desired separation in the rectification zone. In the prior art processes, since the strength of the common desorbent would be limited by the requirement that the strongly adsorbed product not be desorbed in the rectification zone, a considerably larger amount would be required to achieve desorption in the desorption zone, adding significantly to the cost of the separation process. By operation of this embodiment, lower desorption quantities may be realized and this obviously reduces the cost of operating the process. Other variations for carrying out this embodiment could involve a method of separating the two desorbent streams for the purpose of further reducing the preparation cost. For example, in the distillation used to separate the desorbent from the products, one of the desorbent streams could be taken as a sidestream from distillation column 7 and the other desorbent stream taken as an overhead or bottom product. Additionally, if the strong desorbent $D_1$ comprises a component of the weaker desorbent $D_2$, $D_2$ consisting of $D_1$, plus $D_3$, then some $D_1$ could be allowed through valve 8 in FIG. 2 and $D_3$ added to it at the first section of zone 2 to achieve the desired blend of $D_1$ and $D_3$ to produce $D_2$. This then would eliminate the need to distill that portion of $D_1$ which passes through valve 8. Other process sequences which may be envisioned by FIG. 2 and which employ the dual desorbent composition embodiment of the present invention, include distillation of stream 14 in column 33 in the event that same includes some $D_2$ as well as $D_1$ and direction of a portion of stream 34 through valve 9 to section 308 in the event that flow from section 308 to 101 is not desired. The latter application would be employed if there were non-adsorbed components in the feedstream 11 or if it were desired to minimize the length of adsorption zone 3 below draw-off stream 17.

Figure 3:
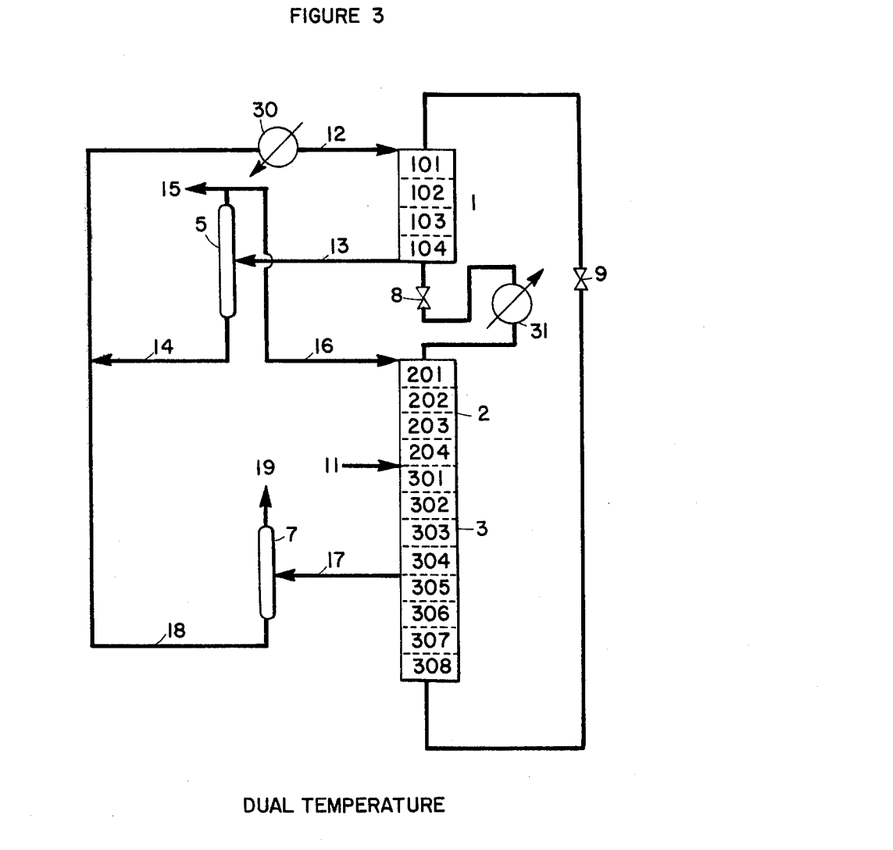

The dual temperature embodiment may be more readily understood with reference to FIG. 3 which shows the desorbent being heated prior to its introduction to desorption zone 1 with a heat exchanger 30 or by other means and removing the residual heat before the desorbent passes the rectification zone through the use of heat exchanger 31. In addition to the flow sequence shown in FIG. 3, the invention may be applied by using other means of carrying out desorption at higher temperatures. Flow sequence in FIG. 3 is otherwise identical to that described above for FIG. 2, except that distillation column 33 and associated stream 34 have been deleted.

Other schemes for operating this embodiment include the operation of distillation colums 5 and 7 in order to produce stream 12 at a sufficiently high temperature to eliminate the need for heat exchanger 30 and heating of the desorption zone by means of a heating medium other than the desorbent such as electric tapes and the like. Additionally, heat exchanger 31 may be eliminated if the heat capacity of zone 1 is sufficient to adequately cool down the desorbent passing through valve 8. It may also prove desirable to carry out flow through valve 9 from section 101 to section 308 such as when there are non-adsorbed components in feedstream 11 and where it is desirable to minimize the length of the adsorption zone 3 below draw-off stream 17. In this applicaton, a portion of stream 12 should be bypassed around heat exchanger 30 to supply normal temperature desorbent to section 308.

Figure 4:
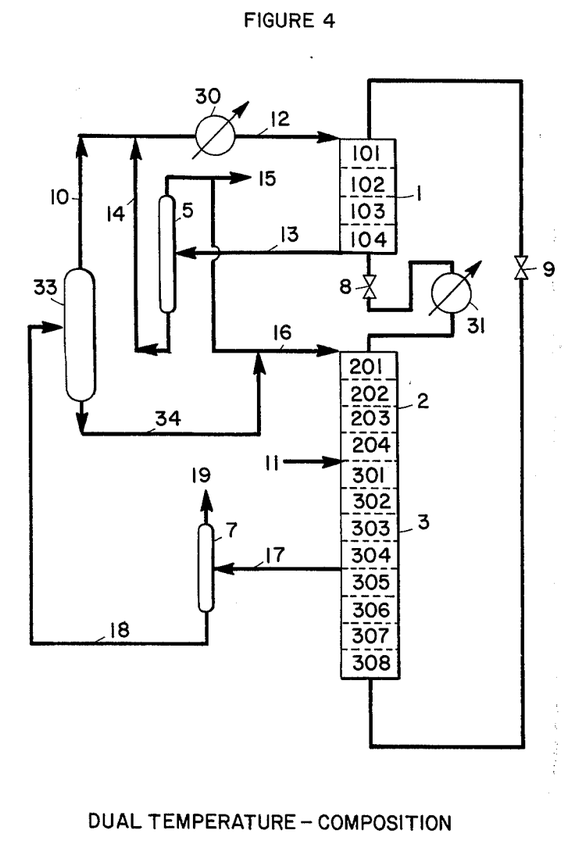

The combined dual temperature and dual composition embodiment may be more readily understood with reference to FIG. 4 which shows the strong desorbent (Stream 10 from distillation column 33 and Stream 14 from distillation column 5) being heated prior to its introduction to desorption zone 1 with a heat exchanger 30. Weak desorbent stream 34 flows into the first section of the rectification zone 2, along with reflux stream 16. Stream 34 is a weaker desorbent than Stream 12 by virtue of both its lower temperature and its lower concentration of eluent in its eluentcarrier composition. Flow sequence in FIG. 4 is otherwise identical to that described above for FIG. 2.

The process of the present invention is further illustrated by the following examples.

EXAMPLE 1

The process as shown in FIG. 1 utilizing distillation columns 5 and 7 to supply a desorbent Stream 12 comprised of 50% meta-diisorpropylbenzene plus 50% paraffin is operated with BaKY sieve at a temperature of 130° C. When a feed (Stream 11) mixture composed of 20% ethylbenzene, 20% paraxylene, 40% metaxylene, and 20% orthoxylene is used in the process, it is found that the volume ratio of desorbent (Stream 14) to product paraxylene (Stream 15) is 8.

EXAMPLE 2

The process as shown in FIG. 2 utilizing distillation column 33 to supply desorbent Stream 12 comprised of 90% meta-diisopropylbenzene plus 10% paraffin and weak desorbent Stream 34 comprised of 25% meta-diisopropylbenzene plus 75% paraffin is operated with BaKY sieve at at temperature of 130° C. When a feed (Stream 11) mixture composed of 20% ethylbenzene, 20% paraxylene, 40% metaxylene, and 20% othoxylene is used in the process, it is found that the volume ratio of desorbent (Stream 14) to product paraxylene (Stream 15) is 6.

EXAMPLE 3

The process as shown in FIG. 3 utilizing a heater (30) to preheat desorbent Stream 12 composed of 25% meta-diisopropylbenzene plus 75% paraffin to 160° C. is operated with BaKY sieve at a temperature of 130° C. and the same feed mixture as Example 22. It is found that the volume ratio of desorbent (Stream 14) to product paraxylene (Stream 15) is 9.

EXAMPLE 4

The process as shown in FIG. 4 utilizing distillation column 33 and preheater 30 to supply a high temperature strong desorbent Stream 12 composed of 90% meta-diisopropylbenzene plus 10% paraffin at 160° C. and a weak desorbent stream composed of 25% meta-diisopropylbenzene plus 75% paraffin at 130° C. is operated with BaKY sieve and the same feed mixture as Example 22. It is found that the volume ratio of desorbent (Stream 14) to product paraxylene (Stream 15) is 4.

EXAMPLES 5 through 21

The process is separately operated according to Examples 1, 2, 3 or 4, (as specified in Table I) with the specified differences underlined. The resulting ratios of desorbent (Stream 14) to product paraxylene (Stream 15) are as shown in Table I.

Examples 1 through 21 show that the use of meta-diisopropylbenzene in any of the various methods of recovering paraxylene from $C_8$ aromatic mixtures in simulated moving beds containing zeolitic adsorbents results in an efficient process.

with a mass of said solid sorbent material, the improvement whih comprises:

I. introducing a desorbent stream containing meta-diisopropylbenzene into the first section of said desorption zone:

II. withdrawing a desorption effluent comprising at least one selectively sorbed component from the last section of said desorption zone;

III. introducing said $C_8$ aromatic feedstream into the first section of said sorption zone; and IV. withdrawing a raffinate effluent comprising a less sorbed component from the last section of said sorption zone.

2. The process of claim 1 wherein said $C_8$ aromatic feedstream comprises paraxylene and ethylbenzene.

3. The process of claim 1 wherein said selectively sorbed component withdrawn in step (II) is paraxylene.

4. The process of claim 1 wherein said desorbent stream employed in step (I) comprises from about 10 to about 99 weight percent of meta-diisopropylbenzene and from about 1 to about 90 weight percent of a diluent selected from the group consisting of from $C_{10}$ to $C_{20}$ paraffins and from $C_6$ to $C_{20}$ saturated cyclic hydrocarbons.

5. In a process for continuously separating, in a liquid phase, the components of a liquid $C_8$ aromatic feedstream wherein at least one of said components is selectively adsorbed by contact with a solid sorbent material material utilizing a simulated countercurrent flow system wherein liquid streams are allowed to flow downward through a desorption zone, a rectification zone and a sorption zone, each zone being serially and circularly interconnected and divided into a plurality of

TABLE I

| Example | Procedure According to Example | Strong Desorbent | | | Weak Desorbent | | | Seive | Ratio (Desorbent/Paraxylene) |
|---|---|---|---|---|---|---|---|---|---|
| | | % MDIPB | % Inert | T °C. | % MDIPB | % Inert | T °C. | | |
| 1[1] | 1 | 50 | 50 | 130 | — | — | — | BaKY | 8 |
| 2 | 2 | 90 | 10 | 130 | 25 | 75 | 130 | BaKY | 6 |
| 3 | 3 | 25 | 75 | 160 | 25 | 75 | 130 | BaKY | 9 |
| 4 | 4 | 90 | 10 | 160 | 25 | 75 | 130 | BaKY | 4 |
| 5[1] | 1 | 50 | 50 | 130 | — | — | — | BaKX | 7.5 |
| 6[1] | 1 | 50 | 50 | 130 | — | — | — | KY | 9 |
| 7 | 2 | 90 | 10 | 130 | 25 | 75 | 130 | BaKX | 5.5 |
| 8 | 2 | 90 | 10 | 130 | 25 | 75 | 130 | KY | 7 |
| 9 | 3 | 25 | 75 | 160 | 25 | 75 | 130 | BaKX | 8.5 |
| 10 | 3 | 25 | 75 | 160 | 25 | 75 | 130 | KY | 10 |
| 11 | 4 | 90 | 10 | 160 | 25 | 75 | 130 | BaKX | 5 |
| 12 | 4 | 90 | 10 | 160 | 25 | 75 | 130 | KY | 4.5 |
| 13[1] | 1 | 25 | 75 | 130 | — | — | — | BaKY | 10 |
| 14[1] | 1 | 75 | 25 | 130 | — | — | — | BaKY | 9 |
| 15[1] | 1 | 90 | 10 | 130 | — | — | — | BaKY | 12 |
| 16 | 2 | 75 | 25 | 130 | 15 | 75 | 130 | BaKY | 7 |
| 17 | 2 | 50 | 50 | 130 | 25 | 75 | 130 | BaKY | 8 |
| 18 | 3 | 50 | 50 | 160 | 50 | 50 | 130 | BaKY | 7 |
| 19 | 3 | 75 | 25 | 160 | 75 | 25 | 130 | BaKY | 8 |
| 20 | 4 | 75 | 25 | 160 | 25 | 75 | 130 | BaKY | 5 |
| 21 | 4 | 50 | 50 | 160 | 25 | 75 | 130 | BaKY | 6 |

[1] In Examples according to procedure in Example 1, only one desorbent used, and its concentration and temperature are given under "Strong Desorbent"

What is claimed is:

1. In a process for continuously separating, in a liquid phase, the components of a liquid $C_8$ aromatic feedstream wherein at least one of said components is selectively adsorbed by contact with a solid sorbent material utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, the improvement which comprises:

(I) introducing a desorbent stream containing from about 10 to about 99 weight percent of meta-diisopropylbenzene and from about 1 to about 90 weight percent of a diluent selected from the group consisting of from $C_{10}$ to $C_{20}$ paraffins and from $C_6$ to $C_{20}$ saturated cyclic hydrocarbons into the first section of said desorption zone;

II. withdrawing a desorption effluent comprising at least one selectively sorbed component from the last section of said desorption zone;

III. introducing said $C_8$ aromatic feedstream into the first section of said sorption zone; and IV. withdrawing a raffinate effluent comprising a less sorbed component from the last section of said sorption zone.

6. The process of claim 5 wherein the amount of meta-diisopropylbenzene is in the range of from about 40 to about 99 weight percent and the amount of said diluent is in the range of from about 1 to about 60 weight percent based on the total desorbent stream.

7. The process of claim 1 wherein said diluent is selected from the group consisting of from $C_{11}$ to $C_{18}$ paraffins, from $C_{11}$ to $C_{18}$ saturated cyclic hydrocarbons and their alkyl derivatives.

8. The process of claim 1 wherein said solid sorbent material is a crystalline aluminosilicate selected from the group consisting of potassium substituted zeolite X, potassium substituted zeolite Y, barium substituted zeolite X, barium substituted zeolite Y, barium and potassium substituted zeolite X and barium and potassium substituted zeolite Y.

9. The process of claim 1 wherein said $C_8$ aromatic feedstream comprises paraxylene and ethylbenzene.

10. The process of claim 9 wherein said selectively sorbed component withdrawn in step (II) is paraxylene.

* * * * *